US006436668B1

(12) United States Patent
Ferreira et al.

(10) Patent No.: US 6,436,668 B1
(45) Date of Patent: *Aug. 20, 2002

(54) PROCESS FOR THE EXPRESSION AND PRODUCTION OF THE RECOMBINANT GROWTH FACTOR PROTEIN (BEGF) DERIVED FROM BEAN 58058 VIRUS (BEV)

(75) Inventors: Paulo C. P. Ferreira; Erna G. Kroon; Flavio G. da Fonseca, all of Belo Horizonte (BR)

(73) Assignee: Universidade Federal de Minas Gerais, Belo Horizonte (BR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/142,138
(22) PCT Filed: Dec. 30, 1997
(86) PCT No.: PCT/BR97/00086
§ 371 (c)(1),
(2), (4) Date: Feb. 12, 1999
(87) PCT Pub. No.: WO98/29549
PCT Pub. Date: Jul. 9, 1998

(30) Foreign Application Priority Data

Jan. 2, 1997 (BR) ............................................. 9700655

(51) Int. Cl.[7] .................. C12N 15/12; C12N 15/18; C12P 21/02; C07K 14/47; C07K 14/475
(52) U.S. Cl. .................. 435/69.1; 435/71.1; 435/252.3; 435/252.33; 530/399; 530/415
(58) Field of Search ................................. 530/399, 415; 435/69.1, 71.1, 252.3, 252.33

(56) References Cited

PUBLICATIONS

Cell, vol. 42, No. 1, Aug. 1985, P. Stroobant et al: "Purification and Characterization of Vaccina Virus Growth Factor", pp. 383–393.

Science, vol. 235, Jan. 16, 1987, G.S. Schultz et al: "Epithelial Wound Healing Enhanced by Transforming Growth Factor–oc and Vaccinia Growth Factor", pp. 350–352.

*Primary Examiner*—Christine J. Saoud
(74) *Attorney, Agent, or Firm*—Young & Thompson (57) ABSTRACT

The present invention describes recombinant growth factor (BEGF) protein isolated from the virus BeAn58058, their corresponding encoding recombinant DNA molecule and the process of production of the recombinant BEGF protein produced through genetic engineering techniques, to be used in human or veterinarian clinical or in research.

8 Claims, 6 Drawing Sheets

Figure 1

FIGURE 2

Seq ID No: 5

MetIleIleArgSerPheAlaAspSerGly

AsnAlaIleGluThrThrSerProGluIle.

ThrAsnAlaThrThrAspIleProAlaIle.

ArgLeuCysGlyProGluGlyAspGlyTyr.

CysLeuHisGlyAspCysIleHisAlaArg.

AspIleAspGlyMetTyrCysArgCysSer.

HisGlyTyrThrGlyIleArgCysGlnHis.

ValValLeuValAspTyrGlnArgSerGlu.

LysProAsnThrThrThrSerTyrIlePro.

SerProGlyIleMetLeuValLeuValGly.

IleIleIleThrCysCysLeuLeuSer.

ValTyrArgPheThrArgArgThrLysLeu.

ProIleGlnAspMet ValValPro

Figure 3

Hydrophilicity profile of protein sequence BEGF
Computed using an average group length of 6 amino acids.

SEQUENCE LISTING

<160> NUMBER OF SEQ ID NOS: 5

<210> SEQ ID NO 1
<211> LENGTH: 30
<212> TYPE: DNA
<213> ORGANISM: BeAn58058 orthopoxvirus

<400> SEQUENCE: 1
cgcaggatcc atatcagatc attcgccgat 30

<210> SEQ ID NO 2
<211> LENGTH: 25
<212> TYPE: DNA
<213> ORGANISM: BeAn58058 orthopoxvirus

<400> SEQUENCE: 2
ccagaagctt tggcacaacc atatc 25

<210> SEQ ID NO 3
<211> LENGTH: 20
<212> TYPE: DNA
<213> ORGANISM: Escherichia coli

<400> SEQUENCE: 3
ttcattaaag aggagaaatt 20

<210> SEQ ID NO 4
<211> LENGTH: 20
<212> TYPE: DNA
<213> ORGANISM: Escherichia coli

<400> SEQUENCE: 4
ctatcaacag gagtccaagc 20

<210> SEQ ID NO 5
<211> LENGTH: 128
<212> TYPE: PRT
<213> ORGANISM: BeAn58058 orthopoxvirus

<400> SEQUENCE: 5

```
Met Ile Ile Arg Ser Phe Ala Asp Ser Gly Asn Ala Ile Glu Thr Thr
  1               5                  10                  15

Ser Pro Glu Ile Thr Asn Ala Thr Thr Asp Ile Pro Ala Ile Arg Leu
             20                  25                  30

Cys Gly Pro Glu Gly Asp Gly Tyr Cys Leu His Gly Asp Cys Ile His
         35                  40                  45

Ala Arg Asp Ile Asp Gly Met Tyr Cys Arg Cys Ser His Gly Tyr Thr
     50                  55                  60

Gly Ile Arg Cys Gln His Val Val Leu Val Asp Tyr Gln Arg Ser Glu
 65                  70                  75                  80

Lys Pro Asn Thr Thr Thr Ser Tyr Ile Pro Ser Pro Gly Ile Met Leu
                 85                  90                  95

Val Leu Val Gly Ile Ile Ile Ile Thr Cys Cys Leu Leu Ser Val Tyr
            100                 105                 110

Arg Phe Thr Arg Arg Thr Lys Leu Pro Ile Gln Asp Met Val Val Pro
        115                 120                 125
```

PROCESS FOR THE EXPRESSION AND PRODUCTION OF THE RECOMBINANT GROWTH FACTOR PROTEIN (BEGF) DERIVED FROM BEAN 58058 VIRUS (BEV)

This application is the national phase of international application PCT/BR97/00086 filed Dec. 30, 1997 which designated the U.S.

TECHNICAL FIELD OF THE INVENTION

The present invention refers to the general field of the technology of DNA recombinant proteins, for the production of the recombinant growth factor (BEGF) of the virus BEAN 58058, to be used in human or veterinarian clinical practices or in research.

BACKGROUND OF THE INVENTION

Growth is a primary, characteristic and fundamental process to any live organism. Although it is usually associated to the initial stages of life, growth is present as a normal property through adult life. This characteristic is shown mainly in the regenerative activities and in the process of programmed recycling of certain cellular types (James, R. & Bradshaw, R. A., Ann. Rev. Biochem. 53: 259–292,1984).

Several factors contribute to stimulating and controlling growth. Among these factors are hormones, neural growth factor, contact to proximal homologous or heterologous cells, interaction with extracellular structures (extracellular matrix), and others. Among the several agents involved in the process of growth regulation a group of proteins became particularly prominent in the last years, being recognized initially as hormones. However, the more careful analysis of these factors demonstrated that they possessed their own characteristics and they came to be studied in a group that was called polypeptide growth factors or simply PGFs. Several characteristics differentiated these proteins from the hormones. Among them was the fact that they are eminently protein molecules. PGFs are transported from the cell through tissue diffusion, following an autocrinous and paracrinous secretion model. To the contrary, hormones present an endocrine secretion model, where the molecules are stored in vesicles and released in the blood stream (James, R. & Bradshaw, R. A., Ann. Rev. Biochem. 53: 259–292, 1984).

The first isolated PGF was the nervous growth factor (NGF) that acts by stimulating the division and differentiation of sympathetic nerves during the development of vertebrates. Another important member of the family of PGFs was discovered, soon after, in consequence of the study of the activity of NGF in mice. This new element was denominated epidermal growth factor (EGF) and it was detected by stimulating the growth of epidermal and epithelial cells. Several other growth factors were described, among them were the growth factors similar to insulin (IGF I and II ), interleukin II (or growth factor of T cells), growth factor derived from platelets (PDGF), transforming growth factor (TGF) erythropoeitin, and others (James, R. & Bradshaw, R. A., Ann. Rev. Biochem. 53: 259–292, 1984; Carpenter, G., Ann. Rev. Biochem. 56: 881–914, 1987; Hillman, R. S. 1990. Hematopoietic agents: Growth factors, minerals and vitamins. in: Gilman, A. G. ;Rall, T. W. ;Niens, A. S. & Taylor, P. (ed.) The pharmacological basis of therapy. 8th edition. Louis Sanford, N.Y., USES., cap. 14, p. 277–1310, 1990).

This superfamily of proteins includes elements structurally similar but with different physiologic functions. The main characteristic is that all these factors possess mitogenic and intrinsic regulatory activities, coordinating the cellular growth. In fact, each PGF possesses specific receptors, located in the plasma membrane of sensitive cells (James, R. & Bradshaw, R. A., Ann. Rev. Biochem. 53: 259–292, 1984). However these concepts are being modified, since today it is known that the receptors of EGF, for example, are present in a wide variety of cellular types, in different tissues. Besides, it is known that the receptors of EGF are responsible for the biological activity of at least two other growth factors similar to EGF: the transforming growth factor (TGF - α) and the growth factor of the vaccinia virus (VGF). The last is a molecule encoded in the genome of the vaccinia virus. Its function is probably associated with the mitotic proliferation of infected and non-infected cells. VGF is responsible for the proliferation activity of the cells through its binding to the receptors in these cells. This phenomenon, well known as molecular mimicry, would create favorable conditions for viral multiplication (Buller, R. M. & Palumbo, G. J., Microbiol. Rev., 55:80–122, 1991; Alamo, A. & Smith, G L, Immune. Today, 16: 474–478, 1995).

The precursor polypeptides of EGF and TGF - α present peptide signal and transmembrane amino acid sequences, suggesting that these factors are located at the cytoplasmic membrane before the cleavage that originates mature molecules. In the same way, the precursor of the VGF protein carries a hydrophobic amino acid in the amino and carboxy terminal that would work as peptide signal and transmembrane sequences respectively (Stroobant,P. et al., Cell, .42: 383–393, 1985). VGF, EGF and TGF - α present groups of residues, mainly cysteines, highly conserved in the mature proteins. These residues, located in homologous sites in these growth factors, are responsible for the formation of three disulfide bridges, which are responsible for the tertiary structure of the molecules and, consequently, for its similar biological actions (Twardzik, D. R. et al., Proc. Natl. Acad. Sci. It USES, 82: 5300–5304, 1985).

The growth factor of the virus BeAn 58058 (BEGF) presents amino acids sequences very similar to the sequence of VGF. There are modifications in the amino acid 17 and 78 in relation to the sequence of VGF. These modifications are changes of a leucine to a serine and an asparagine to lysine, respectively, in the polypeptide sequence of BEGF.

During the 1980's, the physiologic role of PGFs became questioned, once many of these factors became related with processes of cellular transformation and tumor development. PGFs that were initially related to the cellular transformation are EGF, PDGF and mainly the group of TGFs.

Nevertheless. later authors began to evaluate the hypothesis of the therapeutic use of PGFs essentially based on their mitotic properties. The possibility of the therapeutic use of these factors was tested firstly and used in the treatment of hematological diseases. That is the case of the erythropoeitin and of GM-CSF. Such factors have also been used as adjuvant in the treatment of serious infections and in patients submitted to chemotherapy with immune-suppressor drugs. The erythropoeitin is related to the erythropoiesis and, in its absence, the patient has serious anemia. The clinical use of GM-CSF has been tested with success in patients with neutropenia after neoplasia, congenital neutropenia, aplastic anemia, myelodysplastic syndromes and AIDS. GM-CSF acts to increase the granulocyte and macrophages proliferation (Hillman, R. S. 1990. Hematopoietic agents: Growth factors, minerals and vitamins. in: Gilman, A. G. ;Rall, T. W. ;Niens, A. S. & Taylor, P. (ed.) The pharmacological basis of therapy. 8th edition. Louis Sanford, NY, USES., cap. 14, p. 277–1310, 1990).

The therapeutic use of PGFs is still very restricted and their use is still limited to the experimental field. However, the study of growth factors such as EGF, PDGF, IGFs and TGFs open perspectives for the treatment of several illnesses, whose cure depends on tissue regeneration. In fact, Matsuda, N et al. (J. Periodontol. 63:515–525, 1992), tested with efficiency the action of several PGFs (EGF, PDGF, IGF-I and TGF -α) in the proliferation of mouse periodontal fibroblasts. Additionally, an important increase in the synthesis of collagen of these cells was observed. These data evidence the possibility of the use of such factors in the treatment of periodontal diseases.

The topical administration of EGF in small wounds caused by burns or incisions accelerates the epidermal regeneration through the stimulation of the keratinocytes, phenomenon necessary for the healing process. In the same way, the topical administration of TGF-α and VGF accelerated the regeneration of wounds caused by burns of second degree. Additionally, the treatment with TGF-α and VGF was shown to be more efficient than the treatment with EGF, mainly when comparing the amounts used (Schultz et al Science, 235: 350–352, 1987.)

These results illustrate the clinical potential of the several well-known growth factors and they reflect the optimistic perspectives of the use of PGFs in other pathological processes that need inductors of cellular proliferation and regulatory elements of growth.

It is an object of the present invention to describe the recombinant BeAn 58058 growth factor (BEGF) protein isolated from virus BeAn58058, their corresponding encoding recombinant DNA molecule and the process of production of the recombinant BEGF protein produced through techniques of genetic engineering, to be used in human or veterinarian clinical practices or in research.

BRIEF DESCRIPTION OF THE DRAWINGS

These and other objects, features and many attendant advantages of the invention will be better understood upon a reading of the following detailed description when considered in connection with the accompanying drawings herein:

FIG. 1: The vector used for the expression of the recombinant BEGF protein

FIG. 2: Amino acid sequence of the recombinant BEGF protein

FIG. 3: Hydrophilic character of the recombinant BEGF protein

FIG. 4: Detection and selection of the bacterial clones that produced the recombinant BEGF. Selected bacterial samples (*E. coli*, strain M15) were grown in LB medium until the D. O. $_{600}$ of 0.7. The samples were then treated with IPTG, centrifuged and prepared to PAGE analysis in a 15% polyacrylamide gel. Lane 1:Mid range molecular weight marker (Promega, USA). Lanes 2, 4, 6, 8, 10 and 12: clones A10.1, A70.1, F70.1, J70.1 and R.2, respectively, after induction with IPTG. Lanes 3, 5, 7, 9, 11 and 13: same clones without induction with IPTG. The arrow indicates a band that migrates at expected region for the recombinant BEGF.

FIG. 5 : Purification of the recombinant BEGF through nickel chelate column. The selected clone (R.2) was grown in LB medium, induced with IPTG and centrifuged. The bacterial sediment was disrupted and loaded into the column. After that the column was washed with urea 8M pH 8.0 buffer. Protein fractions eluted in pHs of 6.5 to 4.5 were resolved in a 15% SDS-PAGE. Lane 1: fraction eluted with guanidine 6M pH8.0. Lane 2: Fraction eluted with urea 8M pH 8.0. Lane 3: "A" fraction eluted with urea 8M pH 6.5. Lane 4: "B" fraction eluted with urea 8M pH 6.5. Lane 5: "A" fraction eluted with urea 8M pH6.0. Lane 6: "B" fraction eluted with urea 8M pH 6.0. Lane 7: "C" fraction eluted with urea 8M pH 6.0. Lane 8: "D" fraction eluted with urea 8M pH 6.0. Lane 9: "A" fraction eluted with urea pH 5.5. Lane 10: "A" fraction eluted with urea 8M pH5.0. Lane 11: Mid-range molecular size marker (Promega-USA). The arrow indicates a band that migrates at expected region for the recombinant BEGF.

FIG. 6 : c-fos mRNA accumulation in A431 cells. A431 cells were grown in MEM supplemented with 5% bovine fetal serum. After growth, the medium was discarded and cells were treated with several substances. After 30 minutes treatment cells were harvested and total RNA was extracted and resolved in agarose gel (A). The RNA was transferred to nylon membranes and hybridized with labeled c-fos gene probe. The filter was washed and exposed to X-ray film (B). The same filter was also probed with labeled 18S RNA (C). Cells were treated as follows: lane 1: untreated cells; lane 2: cells treated with MEM supplemented with 20% bovine fetal serum; lane 3: cells treated with 8M pH6.0 urea buffer; lane 4: cells treated with "A" fraction eluted with urea 8M pH 6.0 (see FIG. 5, lane 5); lane 5: cells treated with protein loading buffer; lane 6: cells treated with non-induced bacterial extract diluted in protein loading buffer; lane 7: cells treated with IPTG induced bacterial extract diluted in protein loading buffer.

DETAILED DESCRIPTION OF THE INVENTION

The methodology used for the production of the recombinant BEGF protein consists of the cloning and expression, in microorganisms, of the DNA corresponding to the gene that codes the protein BEGF of the virus BeAn 58058 using the methodology of genetic engineering.

In order to better understand this invention the following examples, for illustrative purposes only, are described. The examples illustrate the present invention and are not intended to limit it in spirit or scope. The process can be understood better through the following description in consonance with the examples:

EXAMPLE 1

DNA amplification(1)

The amplification of the fragment corresponding to the BEGF starting from the DNA of the virus BeAn 58058 or starting from the vector that contains the cloned fragment of the gene was carried out using specific oligonucleotides SEQ ID NO:1 5' CGCAGGATCCATATCAGATCATTCGCC GAT 3' and SEQ ID NO:2 5' CCAGAAGCTTTGGCACAACCATATC 3'. Those oligonucleotides were drawn to amplify the DNA region that encodes the corresponding fragment of the BEGF protein and contains the sites for the restriction enzymes BamH 1 and Hind III, in the polymerase chain reaction (PCR).

The reaction was made with Taq polymerase buffer (500 mM KCl, 100 mM Tris-HCl pH 9.0–9.5, 1.5–2.5 mM $MgCl_2$ and 1–2% triton X-100), 0.1–1 U of Taq polymerase (Promega ,E.U.A., Cat. no. M186A), 0.5–1.5 mM $MgCl_2$, 20–50 mM of each nucleotide (dATP,dCTP,dGTP,dTTP) 10–30 pmoles of each primer, and 0.01a 0.1 ng cDNA and $H_20$ q.s.p. 50–100 μl. The reaction was seen in 1–2 cycles at 94–96° C./1–2 min; 53 to 55° C./1–2 min.; 70–72° C./1–2 min; 30 cycles at 94–96° C./1 to 2 min; 36–38° C./1 2min;

70–72° C./1–2 min and more 1 cycle to 94–96° C./1–2 min; 36–38° C./1 to 2 min; 70–72° C./10–15 min.

The fractionation of the DNA was accomplished by electrophoresis in 1.5–2.0% agarose gel. The purification of the amplified DNA was made by cutting out the band of the gel. The band was diluted in 2–3 times the volume of NaI solution (NaI 8M +0.022 M DTT) and sodium phosphate buffer (1M pH 6.0–6.5) and incubated for 5–10 min. to 50–56° C. Glass beads were added to the suspension, mixed, incubated 1–5 min. at room temperature and centrifuged 10–30 seconds. The spheres were washed with ethanol buffer (75% of ethanol, 0.01 M Tris-HCl, pH 7.0–7.6, 0.01 M EDTA, pH 8.0–8.5). The DNA was eluted from the glass spheres with buffer (Tris pH 7.0–7.4 10 mM, 1–3 mM EDTA) at 50–56° C. for 1–5 min.

EXAMPLE 2

Cloning (2)

Figure 1:
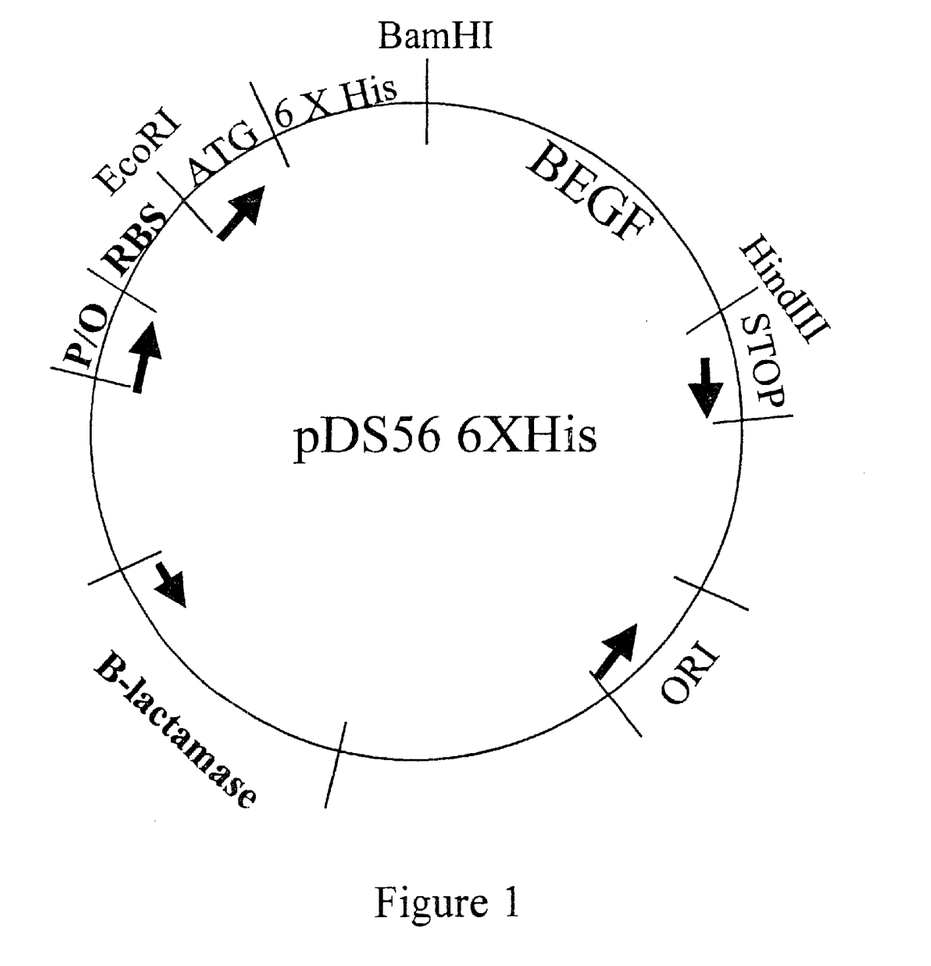

The digestion of the DNA it was firstly treated with enzyme Hind III to in a reaction with 10–20 U of Hind III (Biolabs, England), 3–5 µl buffer (Promega,EUA) and $H_2O$ qsp 30–50 µl. The reactions were incubated at 37° C. for 2–4 h. After this time 10–20 U of Bam HI (Biolabs, England), 5–10 µl of react III (BRL, USA), $H_2O_{dd}$ qsp 50–100 µl were added to the reaction and it was incubated at 37° C. for 2–4 h. For cloning of the DNA fragment in the plasmid PDS-56 (FIG. 1), the digestion of the vector was accomplished with the restriction enzymes Hind III and Bam HI in a reaction that contents vector, 10–20 U of enzyme Hind III (Promega, USA), 2–5 µl (buffer I B (Promega, E.U.A.), $H_2O$ qsp 20–50 µl, with incubation at 37° C. for 2–4 h. Later 10–20 U of the enzyme Bam HI (Promega, USA), 5–10 µl of react III (BRL, E.U.A), $H_2O$ qsp 50–100 µl were added to the reaction and incubated at 37° C. for 2–4 h. The product of this digestion was analyzed by electrophoresis in a 1% TAE-agarose gel. The band corresponding to the digested plasmid was cut out and transferred to a Eppendorf tube (1,5 ml) and purified.

In the ligation reaction 20–50 ng of the insert DNA fragment was added to 5–15 ηg of the vector DNA, 0,5–2,0 U of T4 ligase (Promega, USA), ATP 5 mM (Promega, E.U.A.), ligation buffer (Promega,E.U.A.), $H_2O$ dd to 15 µl, with incubation at 14–16° C. (BOD, FANEN, Brazil) for 12–18 h.

EXAMPLE 3

Transformation (3)

The bacterial transformation was done with *Escherichia coli*. The volume of the ligation reaction was completed to 40–60 µl with buffer (Tris 10 mM pH 7.2–7.4, EDTA 1 mM) and added to 100 µl of suspension of competent bacteria. The tubes were slightly rotated and immediately incubated on ice bath 20–40 min , submitted to a thermal shock at 40–42° C. for 1–3 min. and again on ice bath for 20–40 seconds. LB medium (Bacto triptona 1% p/v, extract of yeast 0.5% p/v, NaCl 171 mM) without antibiotic was added at double volume and incubated at 37° C. for 1–2h. The bacteria were pelleted, homogenized in LB and inoculated in Petri plates with LB agar (agar 1.5% p/v, yeast extract 0.5% p/v, triptone 0.1% p/v, NaCl 0.5% p/v pH 7.2–7.5) with 50–200 µg/ml ampicillin and 20–100 µg/ml kanamycin. The plates were incubated at 37° C. for 15–24 h. Positive clones were selected by being grown in LB with 50–200 µg/ml ampicillin and 20–100 µg/ml kanamycin at 37° C. under agitation for 15–20 h. After incubation a PCR using specific primers of the vector (for amplification of the area corresponding to insert) was the primer (sense) SEQ ID NO:3 5'-TTCATTAAAGAGGAGAAATT-3' and primer (antisense) SEQ ID NO:4 5'-CTATCAACAGGAGTCCMGC-3'.

The reaction was made with Taq. polymerase buffer10 X (KCl 500 mM, Tris-HCl 100 mM pH 9.0–9.5, $MgCl_2$ 15–25 mM and triton X-100 1–2%), 0.5–1.0 U of Taq polymerase (Promega, USA), 0.5–1.5 mM $MgCl_2$, 20–50 mM of each nucleotide (dATP, dCTP, dGTP, dTTP), 10–30 pmoles of each primer, 0.5–1µl of bacterial suspension and $H_2O$ dd sterile to 20–40 µl. The reaction was processed with 1–3 cycles of 94–96° C./5min., 50–55° C./1–2 min., 70–72° C./30 cycles of 94–96° C./30–45 seg., 45–50° C./–45 seg., 70–72° C./30–45 seg and 1 cycle of 94–96° C./1–2 min., 45–50° C./1–2 min., 70–72° C./10–15 min. The product of this reaction was fractionated through 1–2%.agarose gel electrophoresis.

EXAMPLE 4

Sequencing (4)

Figure 2:
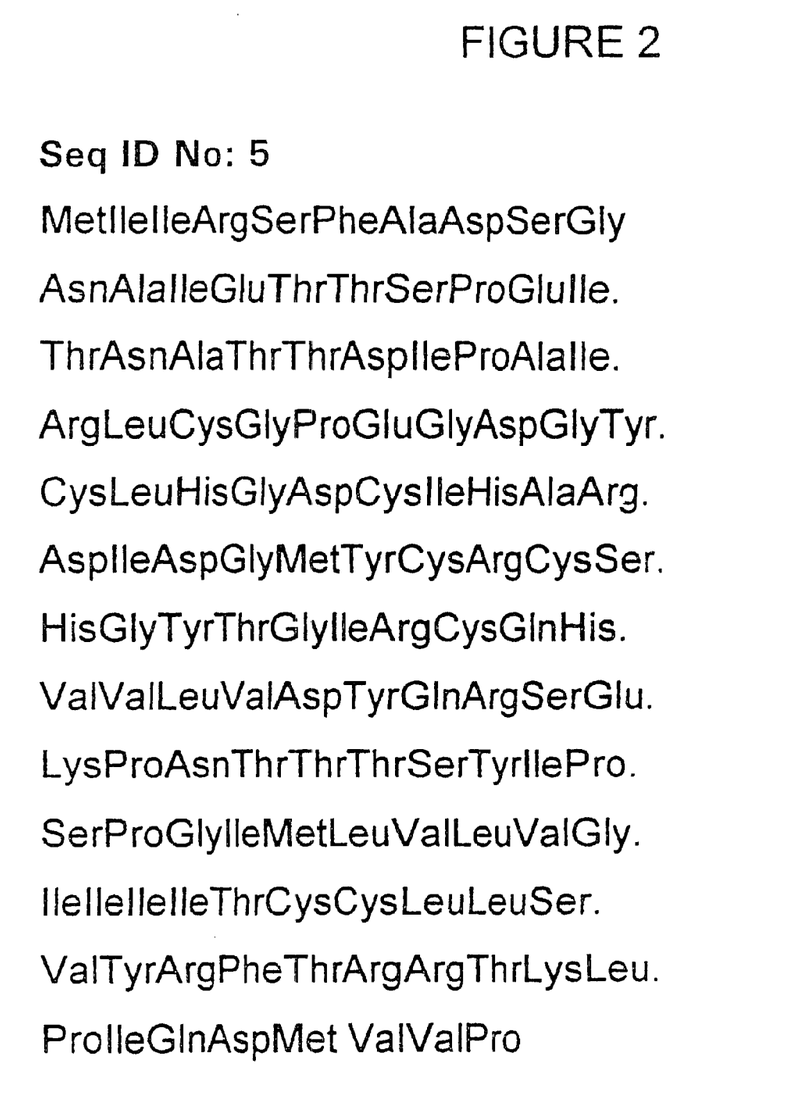
Figure 3:
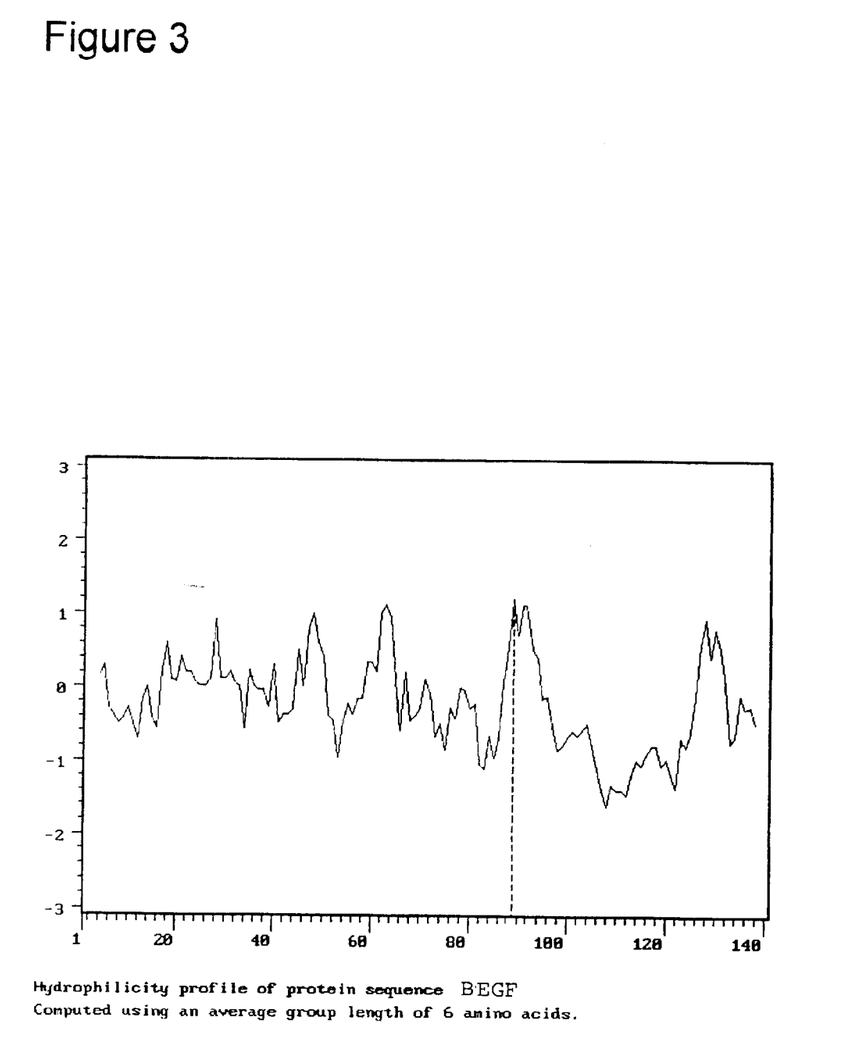

The positive clones were sequenced to confirm the sequence of FIG. 2 and present the hydrophobicity profile as showed in FIG. 3.

EXAMPLE 5

Protein production (5)

Figure 4:
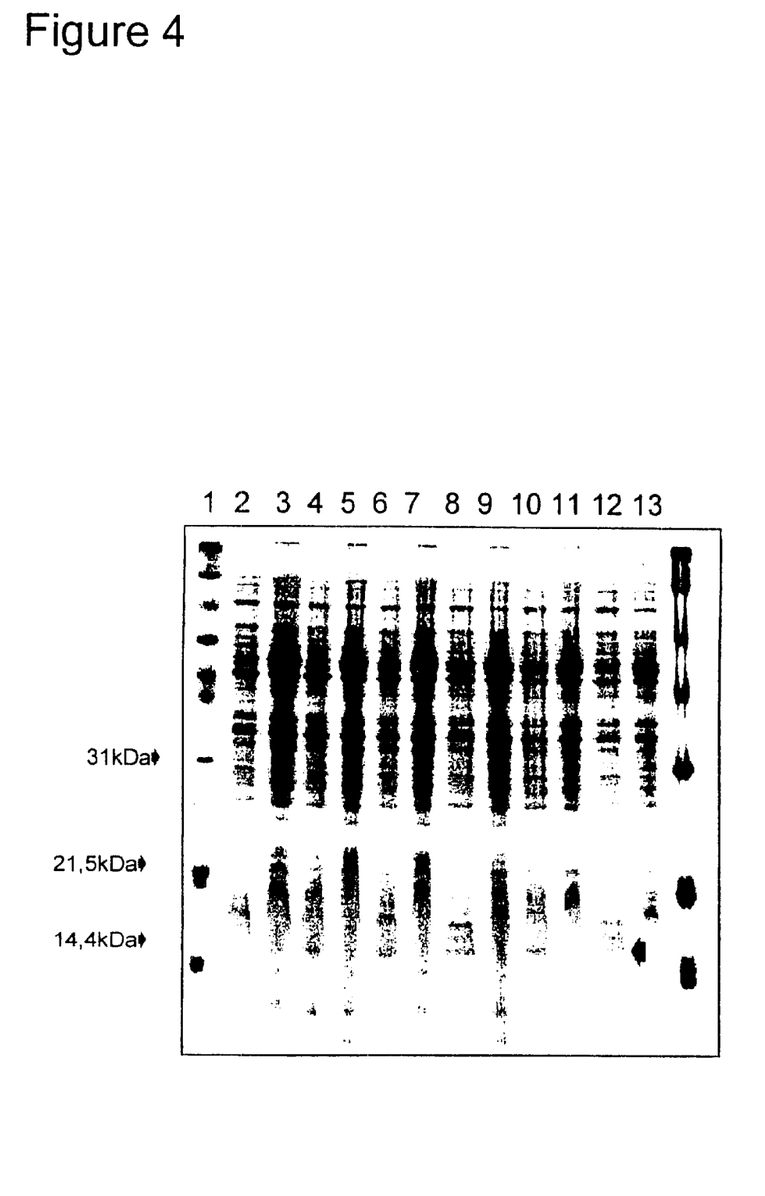

The positive clones were used for the production of the protein and they were grown in LB medium with 50–200 pg/ml ampicillin and 50–200 of kanamycin µg/ml and incubated at 37° C. under agitation until the optical density (OD 600 nm) of 0.5–0.7. Then, for the induction of the protein, IPTG (Isopropyl- (-D-thiogalacoside) to 0.2–0.4 M was added and incubated for 3–5 h. The culture was centrifuged, the supernatant was discarded and the pellet homogenized in buffer A (Guanidine-HCl 5–6 M, sodium phosphate 0.1–0.2 M, Tris 0.01–0.02 M pH 7.8–8.0) with agitation for 1–2 h. A polyacrylamide gel shows the expression in the bacteria. (FIG. 4)

EXAMPLE 6

Figure 5:
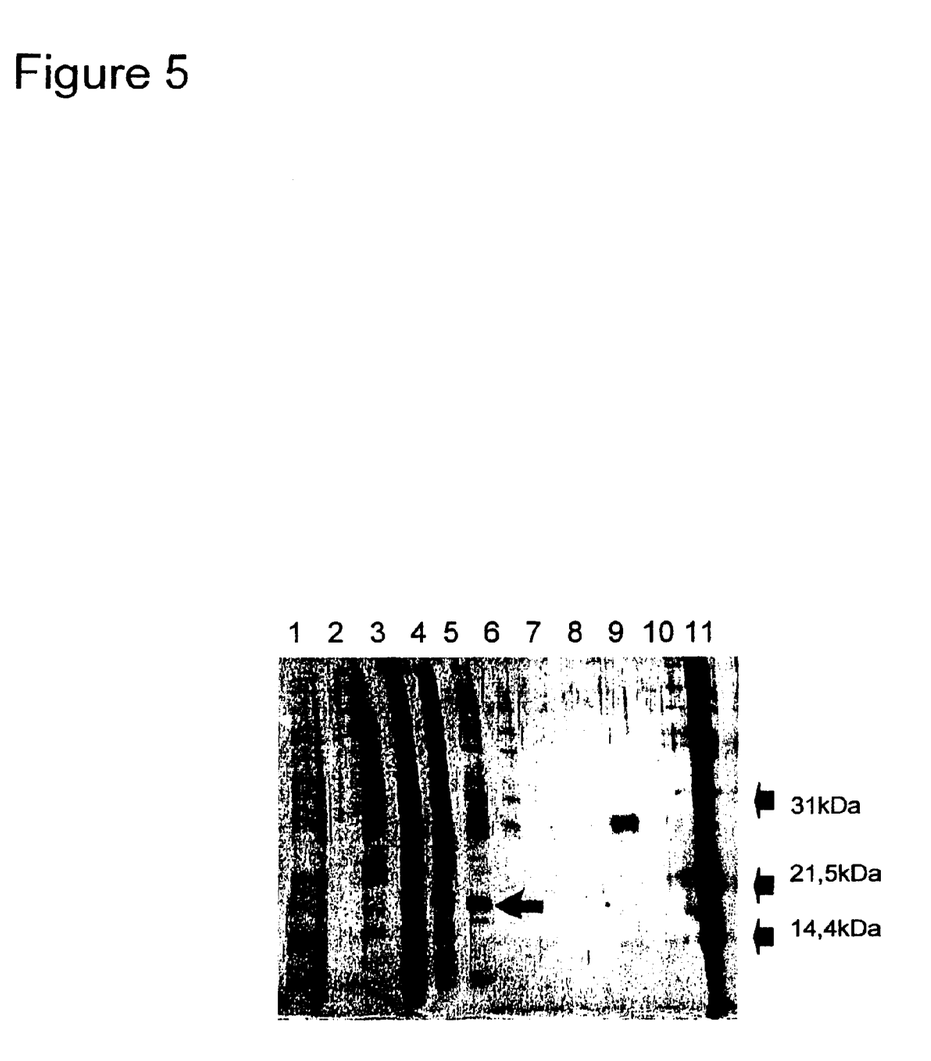
Figure 6:
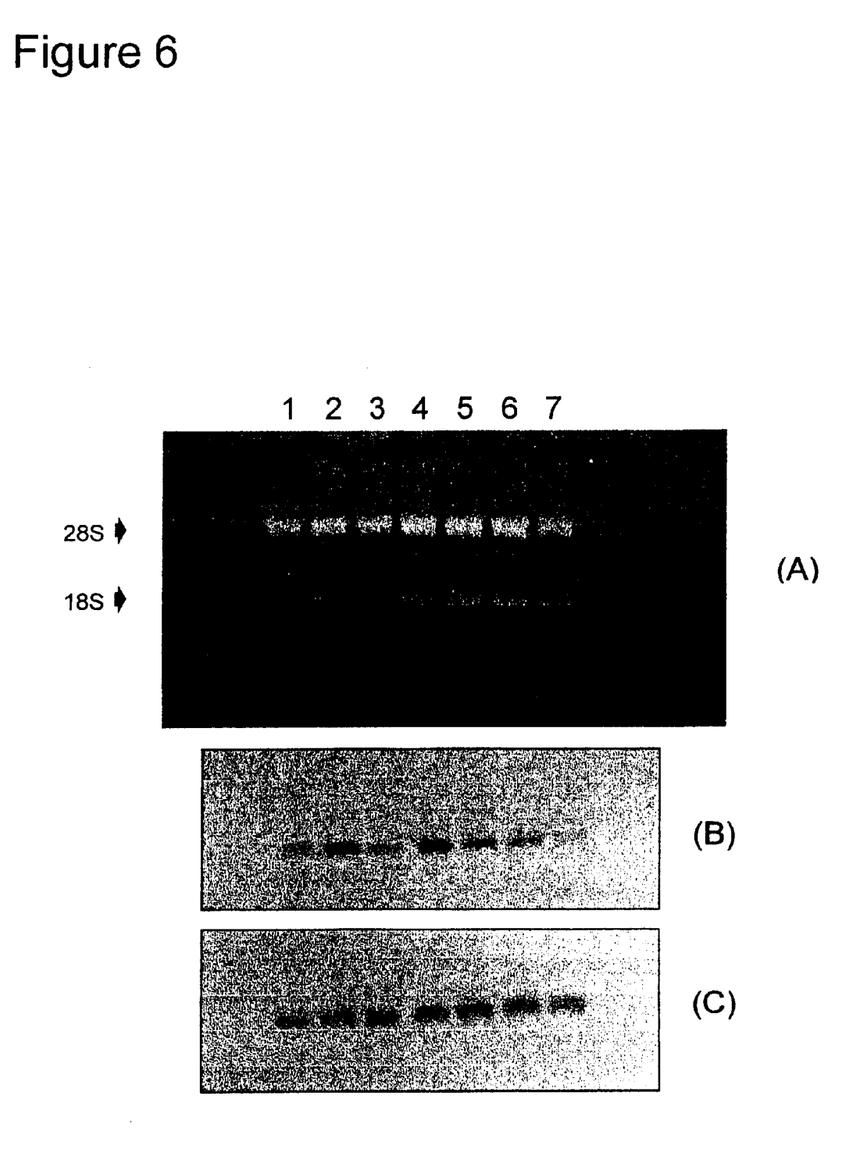

Protein purification (6) After it was centrifuged the supernatant was applied to a column with Ni-NTA (nickel chelate) resin. For the purification of the protein the column was washed sequentially with buffer A, buffer B (Urea 7–8 M, phosphate of sodium 0,1–0,2 M, Tris 0.01–0.02 M pH 7.8–8.0) and with buffer C (Urea 7–8 M, phosphate of sodium 0.1–0.2 M, Tris 0.01–0.02 M pH 7.0–7.2). The protein was eluted with buffer D (Urea 7–8 M, sodium phosphate 0.1–0.2 M, Tris 0.01–0.02 M pH 5.0–5.2) and sequentially with Urea 7–8 M, phosphate of sodium 0.1–0.2 M, Tris 0.01–0.02 M pH 40–4.2; fractions were collected and 50µl of each fraction was diluted v/v in sample buffer, heated for 10 min. and submitted to electrophoresis in polyacrylamide gel (SDS-PAGE). The gel was analyzed for the presence of the fraction that just contained the band corresponding to the purified recombinant BEGF (FIG. 5) and the biological activity was measured in A431 cells (FIG. 6)

While the present invention has been described in connection with examples, it will be understood that modifications and variations apparent to the person of ordinary skill in the art are within the scope of the present invention.

What is claimed is:

1. A process for preparing a BEGF polypeptide, comprising:

introducing a nucleic acid encoding for a protein of SEQ ID NO:5 into a host cell, and culturing said cell under conditions suitable to effect expression of said nucleic acid and to produce said polypeptide.

2. The process according to claim 1, further comprising isolating said peptide.

3. The process according to claim 1, wherein said polypeptide is isolated by applying said polypeptide to a nickel chelate resin.

4. The process according to claim 1, wherein said host cell is a bacterium.

5. The process according to claim 4, wherein said bacterium is *Escherlchia coli*.

6. A process for preparing a BEGF polypeptide, comprising:

introducing a nucleic acid encoding for a protein of SEQ ID NO: 5 into a host cell, said host cell being *E.coli*, culturing said cell under conditions suitable to effect expression of said nucleic acid and to produce said polypeptide, and isolating said polypeptide by applying said polypeptide to a nickel chelate resin.

7. An isolated protein comprising the amino acid sequence of SEQ ID NO: 5.

8. The isolated protein according to claim 7, consisting of the amino acid sequence of SEQ ID NO: 5.

* * * * *